United States Patent [19]

Muller

[11] Patent Number: 4,899,742
[45] Date of Patent: Feb. 13, 1990

[54] ROTARY SCALPEL BLADE AND BLADE PROTECTOR STRUCTURE

[75] Inventor: George H. Muller, Apt. 508 M2, 1945 Gulf of Mexico Dr., Longboat Key, Fla. 34228

[73] Assignees: Joseph J. Berke, Detroit, Mich.; George H. Muller, Longboat Key, Fla. ; a part interest

[21] Appl. No.: 23,651

[22] Filed: Mar. 9, 1987

Related U.S. Application Data

[63] Continuation-in-part of Ser. No. 422,847, Sep. 24, 1982, Pat. No. 4,791,928.

[51] Int. Cl.$^4$ ............................................. A61B 17/32
[52] U.S. Cl. ...................................... 606/180; 30/319; 30/286; 30/296 A; 30/357; 30/298.4
[58] Field of Search ........... 128/305, 317, 310, 303 R, 128/754, 753, 755; 30/292, 319, 307, 347, 276, 296 A, 286, 357, 346; 17/67, 29; 604/22

[56] References Cited

U.S. PATENT DOCUMENTS

| | | | |
|---|---|---|---|
| 1,120,270 | 12/1914 | Brussolo | 30/347 X |
| 1,321,215 | 11/1919 | Kollar | 30/319 |
| 1,467,006 | 9/1923 | Murray | 30/319 |
| 1,636,722 | 7/1927 | Thibaudeau | 30/347 X |
| 2,918,165 | 12/1959 | Paulick | 30/286 X |
| 3,126,889 | 3/1964 | Blumenfeld | 128/303 R |
| 3,929,044 | 12/1975 | Beauchet | 30/357 X |
| 4,111,206 | 9/1978 | Vishnevsky et al. | 128/305 |
| 4,140,123 | 2/1979 | Curutchet | 128/314 |
| 4,611,400 | 9/1986 | Drake | 30/353 |

FOREIGN PATENT DOCUMENTS

| | | | |
|---|---|---|---|
| 1138195 | 10/1962 | Fed. Rep. of Germany | 30/347 |
| 994256 | 11/1951 | France | 128/314 |

Primary Examiner—Michael H. Thaler

[57] ABSTRACT

Rotary scalpel blade and blade protector structure. The rotary scalpel blade in one embodiment is circular and has a sharpened outer periphery and an opening through the center thereof for securing the blade to means for rotating the blade. In modifications of the circular scalpel blade the sides of the scalpel blade may be concave, depressed or flat with an annular groove around the outer periphery thereof. The rotary scalpel blade may also be a linear radial scalpel blade sharpened on one or both edges. The blade protector structure in one embodiment includes a disc having a disc shaped pocket in the center thereof split centrally to receive a scalpel blade, held together with a living hinge and locked in closed position by a split cylinder positioned over a cylindrical flange on one side of the blade protector. In another embodiment, the blade protector is a plastic envelope including a recess open on one side and having slots extending thereacross with a reduced opening at the top for receiving blades to be protected. A further embodiment of the blade protector is a flat, flexible sheet having a tacky adhesive on one side thereof.

5 Claims, 8 Drawing Sheets

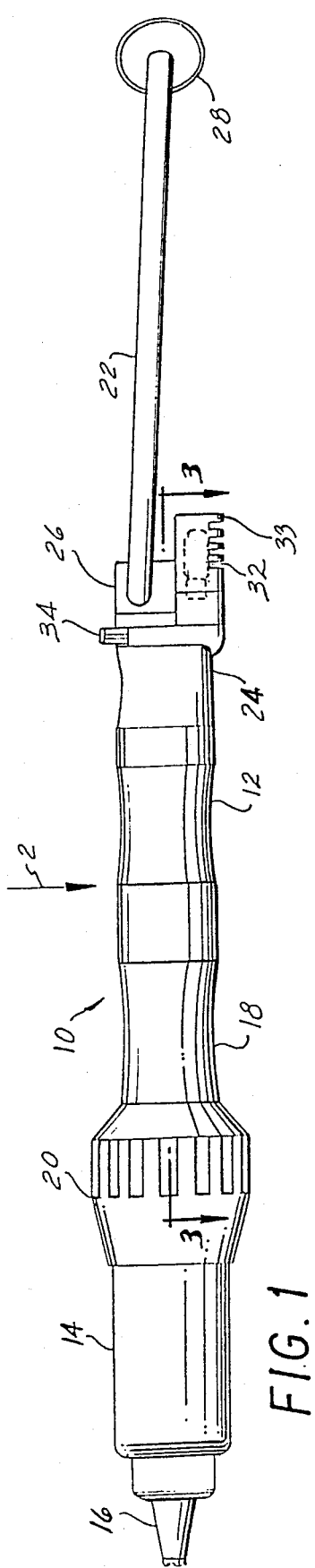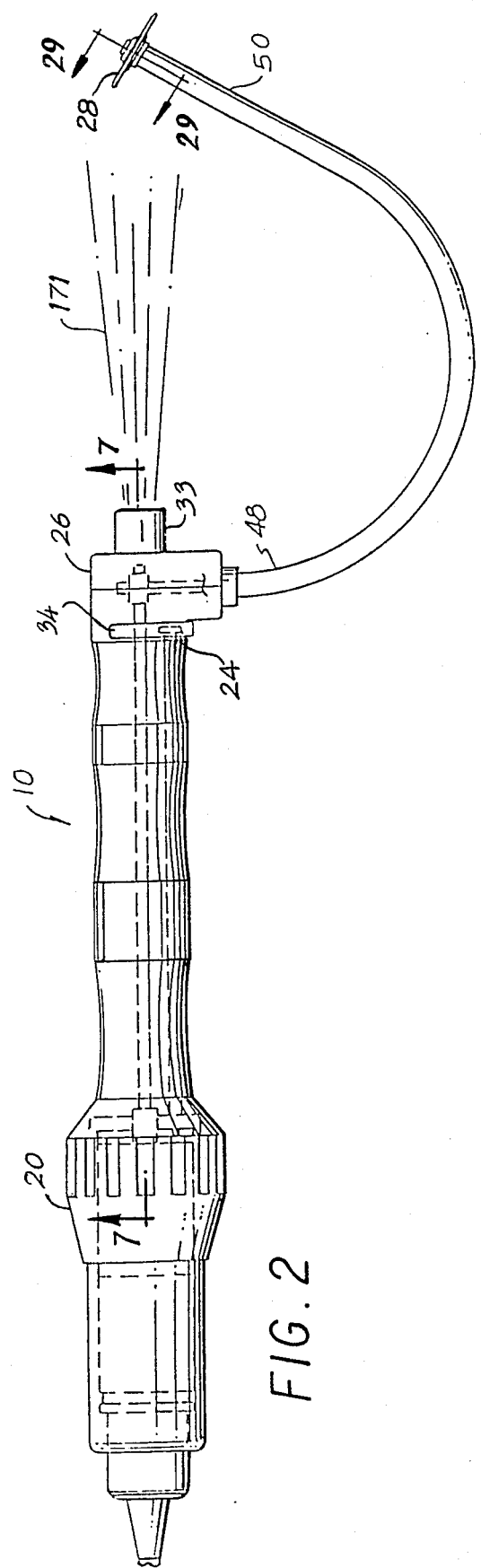
FIG. 1
FIG. 2

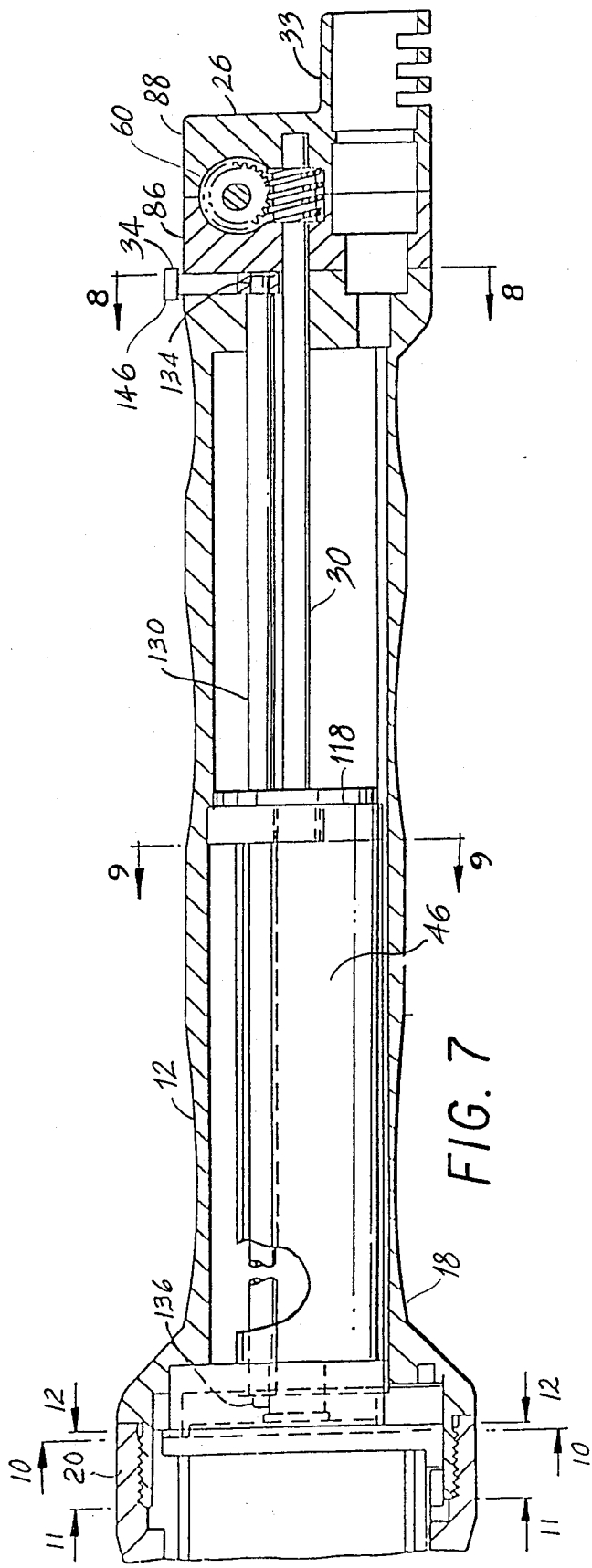
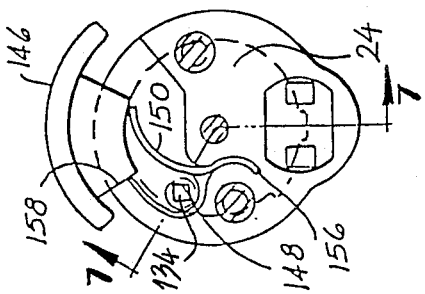
FIG. 7
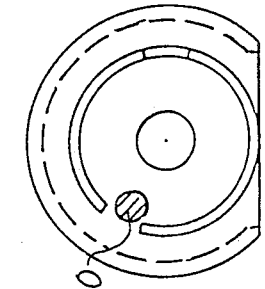
FIG. 8
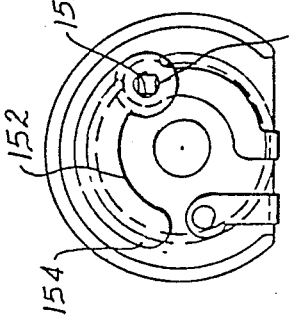
FIG. 9
FIG. 10
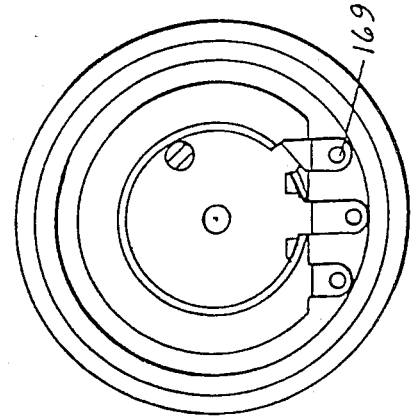
FIG. 11
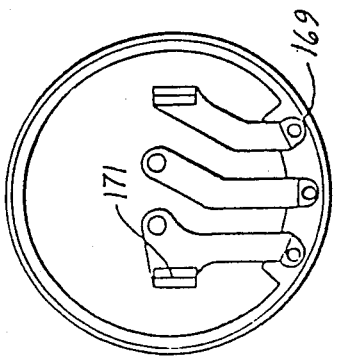
FIG. 12

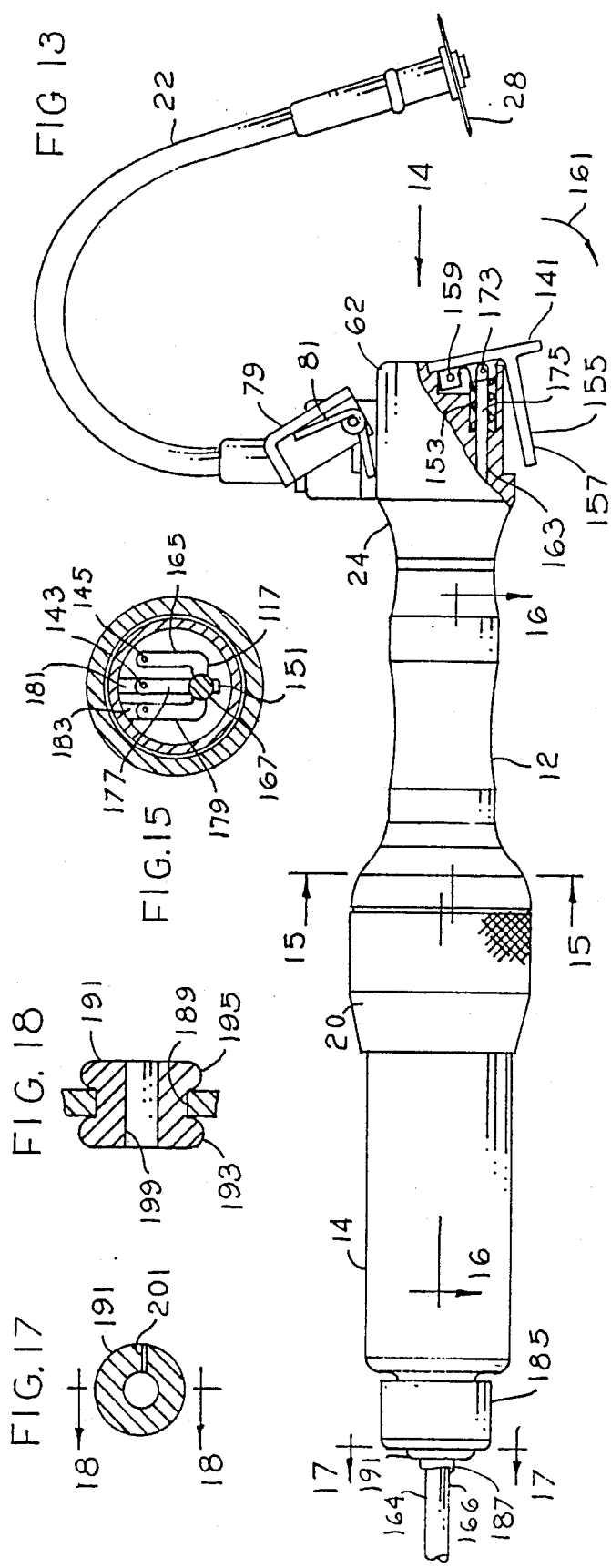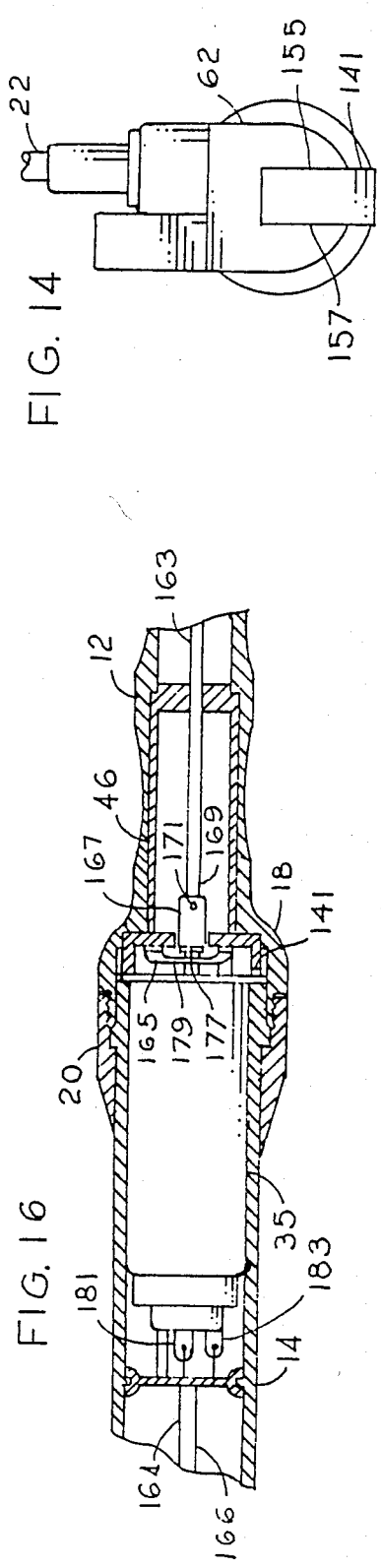

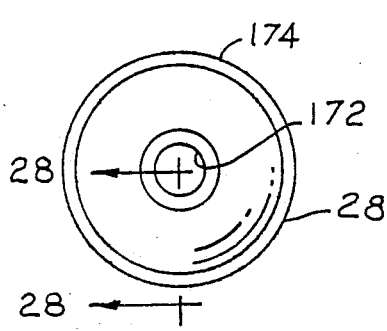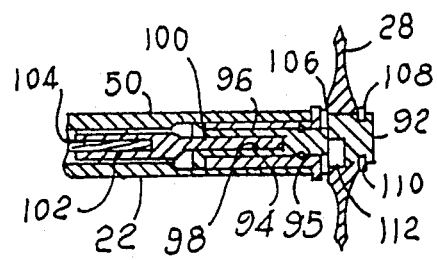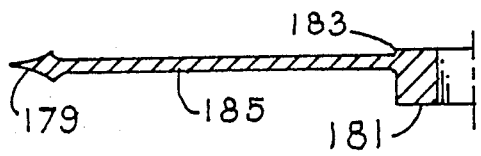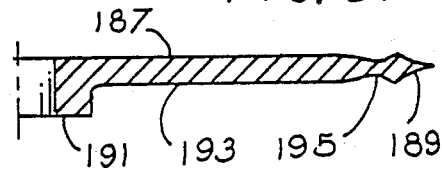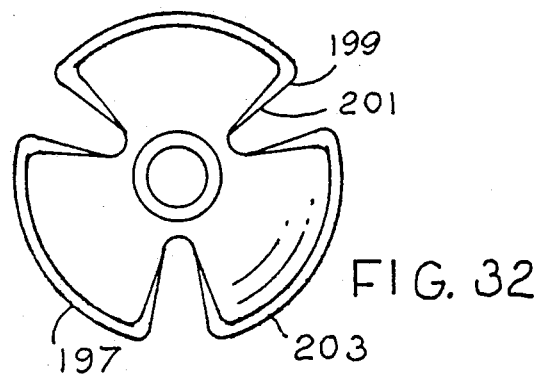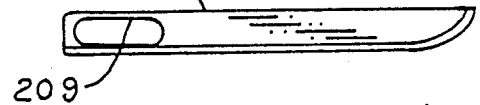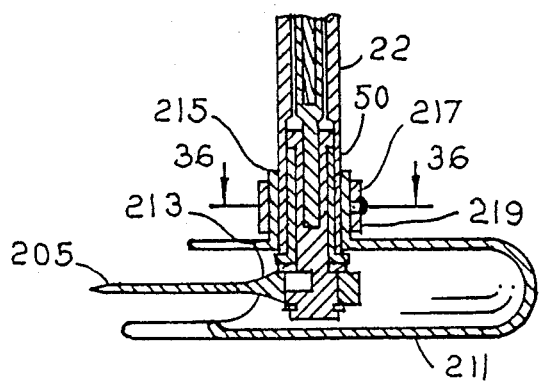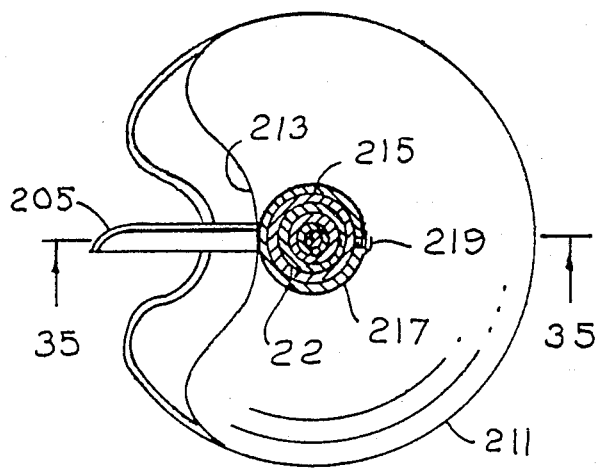

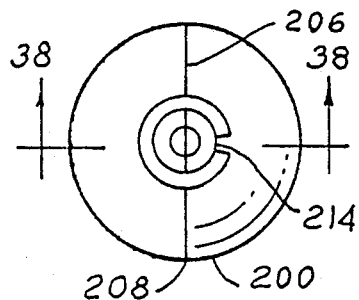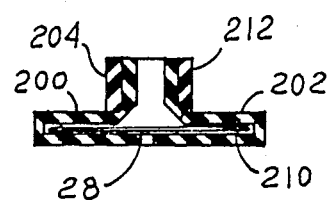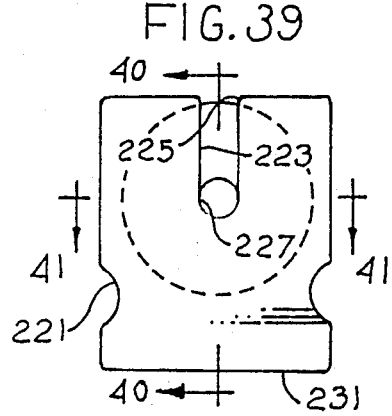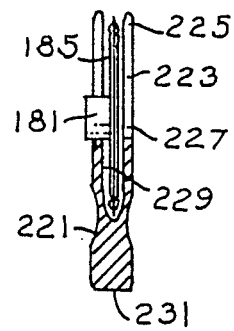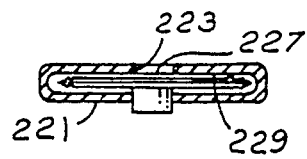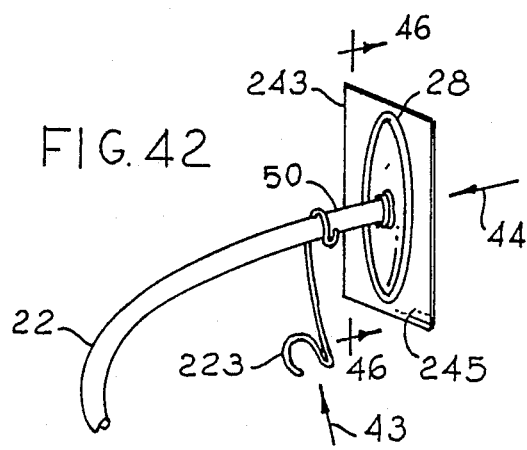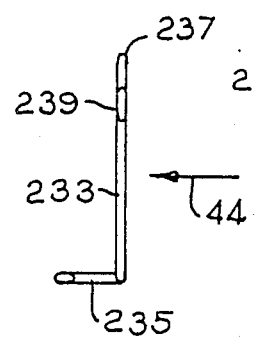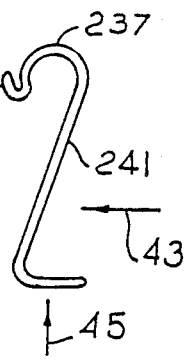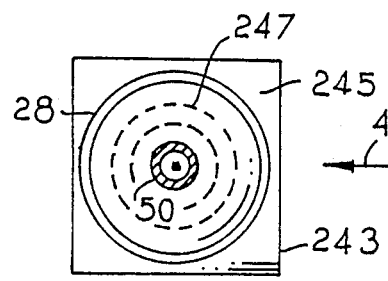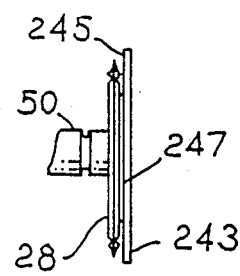

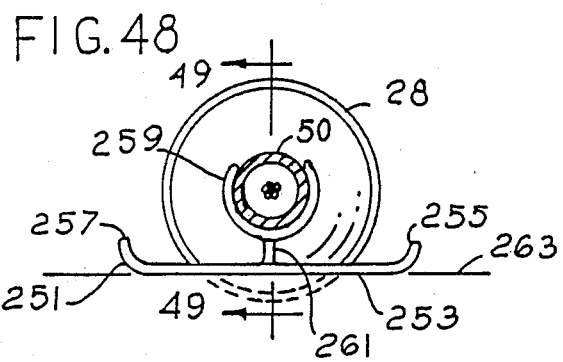
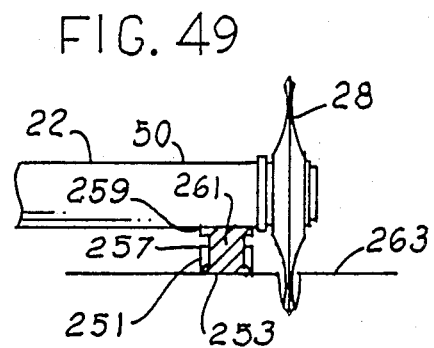
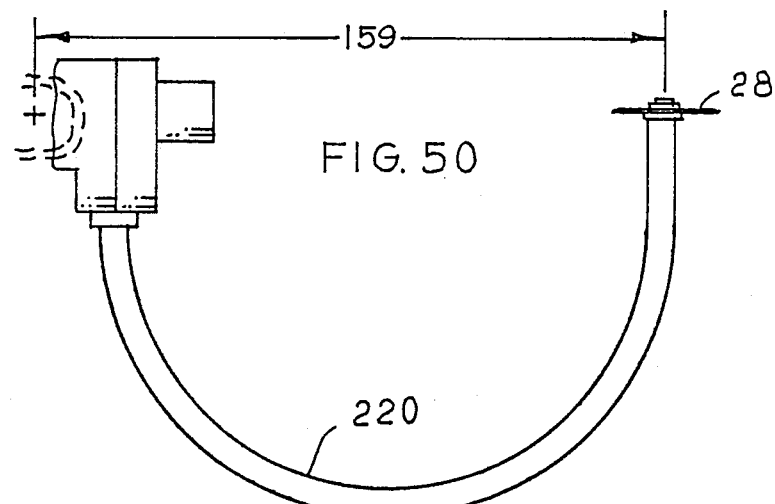
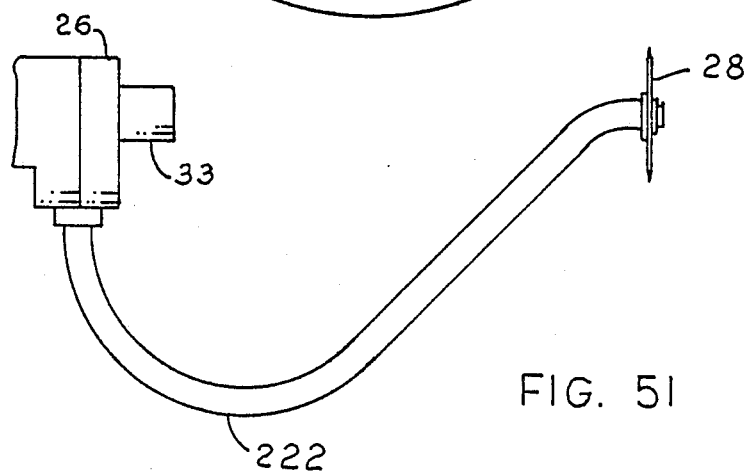
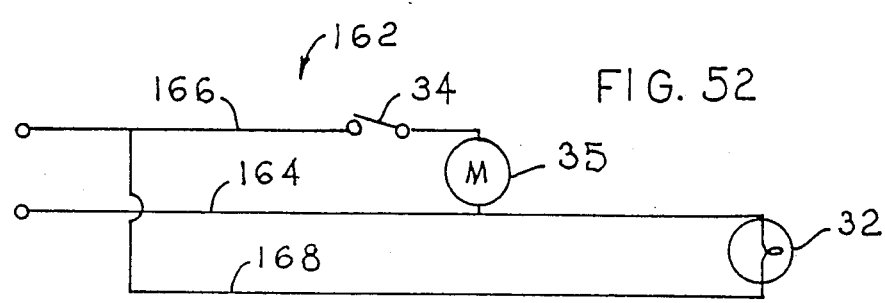

4,899,742

ROTARY SCALPEL BLADE AND BLADE PROTECTOR STRUCTURE

RELATED APPLICATIONS

This application is a continuation-in-part of patent application Ser. No. 422,847, filed Sept. 24, 1982, now U.S. Pat. No. 4,791,928.

BACKGROUND OF THE INVENTION

1. Field of the Invention

The invention relates to surgery and refers more specifically to a powered rotary scalpel structure and method whereby an incision is made with a rotating circular scalpel blade having a circumferential speed preferably in the range of 4 to 7 centimeters per second so that scar tissue is minimized, and to a specific rotary scalpel blade and blade protector structure for use therewith.

2. Description of the Prior Art

In the past, surgical incisions have generally been manually made with a straight scalpel used linearly which is essentially a straight sharp knife. With such structure, and particularly at the start of an incision, the material cut, i.e. human skin, is essentially crushed rather than cut as it would be by a moving blade as it is later during the making of an incision as the surgeon moves the blade more rapidly across the area in which the incision is required.

It is well known that with such scalpels and such procedures that in the crushed area, considerably more scar tissue will build up on healing of the incision than in the area where the scalpel is at the desired cutting depth and is moving along the incision plane while the incision is being made. Scar tissue, i.e. eversion is undesirable and should be minimized.

SUMMARY OF THE INVENTION

The rotary scalpel structure of the invention for practicing the method of the invention is a power driven rotary scalpel.

The power driven rotary scalpel includes a hollow cylindrical handle, a housing at one end of the handle for receiving an electric motor and electrical power for the rotary scalpel, a blade support arm at the other end of the handle on which a circular scalpel blade is mounted for rotation and means for driving the rotary scalpel blade through the support arm and handle from the motor including a gear box.

In accordance with the invention, the blade support arm is releasably secured to the handle by support arm securing structure including rotating pin structure, which pin structure may be bowed to reduce tolerance requirements. Alternatively, the pin of the rotating pin structure may include an eccentric portion. Also with one modification of the support arm securing structure the support arm may be secured to the handle of the rotary scalpel in different angular positions with respect thereto.

The power driven rotary scalpel also includes a light for illuminating the area of the blade which light is always on when power is applied to the power driven rotary scalpel and indicates a power on condition.

Also, a wire protector is provided in accordance with the invention to protect electrical leads as they pass into and out of the handle within which the motor is housed.

Remote switch structure and a modification thereof is further provided for turning on the electric motor at the rear of the handle from the front of the handle.

The structure of the invention further includes a rotary scalpel blade having concave sides for reducing friction between the blade and tissue being cut thereby. Modified blade structures in accordance with the invention include a depressed side, circular blade structure and a flat side, circular blade structure with an annular recess at the outer periphery thereof. Part circular and radial linear, rotating scalpel blades are also contemplated in accordance with the invention.

A hollow flat disc protector for rotary circular scalpel blades including a living hinge and an axially split resilient cylinder closure therefore is also provided in accordance with the invention, along with modified blade protectors including a flat slotted envelope type rotary circular blade protector and a sticky paper blade protector.

The rotary scalpel structure of the invention further includes a support stand for sterilization of the support arm and circular blade secured thereto in the form of a bent wire or narrow strip and a sled like control for limiting the depth of cut possible with the rotary scalpel structure of the invention.

The method of the invention includes rotating a circular scalpel blade and drawing it across tissue in which an incision is desired. In the method of the invention, the rotary scalpel blade is rotated at a speed such that the circumferential speed of the rotary scalpel blade is between 4 and 7 centimeters per second. Also, in accordance with the method of the invention, the depth of cut with the rotating scalpel is limited and the scalpel blades are protected during sterilization or during shipment.

BRIEF DESCRIPTION OF THE DRAWINGS

FIG. 1 is a side view of the power driven rotary scalpel constructed in accordance with the invention for performing the method of the invention.

FIG. 2 is a top view of the rotary scalpel illustrated in FIG. 1.

FIG. 7 is an enlarged, partial longitudinal section of the rotary scalpel shown in FIG. 1 taken substantially on the line 7—7 in FIG. 8.

FIG. 8 is a front end view of the handle of the rotary scalpel shown in FIG. 1 taken substantially on the line 8—8 in FIG. 7.

FIG. 9 is a front end view of the guiding and bearing member of the rotary scalpel shown in FIG. 1 taken substantially on the line 9—9 in FIG. 7.

FIG. 10 is a back end view of the guiding and bearing member of the rotary scalpel shown in FIG. 1 taken substantially on the line 10—10 in FIG. 7.

FIG. 11 is a back end view of the handle of the rotary scalpel shown in FIG. 1 taken substantially on the line 11—11 in FIG. 7.

FIG. 12 is a front end view of the motor housing of the rotary scalpel shown in FIG. 1 taken substantially on the line 12—12 in FIG. 1.

FIG. 13 is a partly broken away top view of a modification of the rotary scalpel structure shown in FIG. 1 illustrating modified support arm securing and switching structure.

FIG. 14 is a partial end view of the rotary scalpel structure shown in FIG. 13, taken in the direction of arrow 14 in FIG. 13.

FIG. 15 is a section view of the modified rotary scalpel structure shown in FIG. 13, taken substantially on line 15—15 in FIG. 13.

FIG. 16 is a longitudinal section view of a portion of the rotary scalpel structure illustrated in FIG. 13 taken substantially on the line 16—16 in FIG. 13.

FIG. 17 is an enlarged partial section view of the rotary scalpel structure shown in FIG. 13, taken substantially on the line 17—17 and showing the electric wire protector of the invention.

FIG. 18 is a partial section view of the rotary scalpel structure shown in FIG. 13, taken substantially on the line 18—18 in FIG. 17.

FIG. 27 is a side view of a circular scalpel blade constructed in accordance with the invention.

FIG. 28 is an enlarged partial section view of the scalpel blade illustrated in FIG. 27, taken substantially on the line 28—28 in FIG. 27.

FIG. 29 is an enlarged section of the free end of the blade support arm and circular scalpel blade of the rotary scalpel structure illustrated in FIG. 1, taken substantially on the line 29—29 in FIG. 2 illustrating rotary mounting means for the scalpel blade illustrated in FIG. 27.

FIG. 30 is a partial radially extending section view of modified circular scalpel blade structure similar to FIG. 28.

FIG. 31 is a another partial radially extending section view of modified circular scalpel blade structure similar to FIG. 30.

FIG. 32 is a plan view of modified part circular scalpel blade structure constructed in accordance with the invention similar to FIG. 27.

FIG. 33 is a plan view of a linear radial blade for use in unidirectional rotary scalpel structure in accordance with the invention having one sharp edge.

FIG. 34 is a plan view of a modification of the linear radial blade illustrated in FIG. 33 having two sharp edges for use with bidirectional rotary scalpel structure.

FIG. 35 is a section view of modified circular scalpel structure constructed in accordance with the invention utilizing a radially extending linear blade such as shown in FIGS. 33 and 34 and including a semiperipheral blade guard in conjunction therewith.

FIG. 36 is a view of the modified circular scalpel structure shown in FIG. 35 taken substantially on the line 36—36 in FIG. 35.

FIG. 37 is a top view of blade protector structure constructed in accordance with the invention for the scalpel blade illustrated in FIG. 27.

FIG. 38 is a cross section of the blade protector structure illustrated in FIG. 37 taken substantially on the line 38—38 in FIG. 37.

FIG. 39 is a plan view of modified blade protector structure for circular scalpel blades constructed in accordance with the invention.

FIG. 40 is a section view of the blade protector structure illustrated in FIG. 39 taken substantially on the line 40—40 in FIG. 39.

FIG. 41 is a section view of the blade protector structure illustrated in FIG. 39 taken substantially on the line 41—41 in FIG. 39.

FIG. 42 is a perspective view of a blade support arm, including a circular scalpel blade, secured thereto constructed in accordance with the invention supported on a blade support arm stand and showing modified blade protector structure both constructed in accordance with the invention.

FIG. 43 is a side view of the blade support arm stand shown in FIG. 42 taken substantially in the direction of arrow 43 in FIGS. 42 and 44.

FIG. 44 is an end view of the blade support arm stand shown in FIG. 42 taken substantially in the direction of arrow 44 in FIGS. 42 and 43.

FIG. 45 is a bottom view of the blade support arm stand shown in FIG. 42 taken substantially in the direction of arrow 45 in FIG. 44.

FIG. 46 is a partial section view of the blade support arm structure and modified partially sticky blade protector structure illustrated in FIG. 42 taken substantially on the line 46—46 in FIG. 42.

FIG. 47 is a side view of the modified blade protector structure illustrated in FIG. 46 taken substantially in the direction of arrow 47 in FIG. 46.

FIG. 48 is a side elevation view of depth limiting structure in combination with rotary circular scalpel structure in accordance with the invention.

FIG. 49 is a section view of the depth limiting structure illustrated in FIG. 48 taken substantially on the line 49—49 in FIG. 48.

FIG. 50 is a top view of a modified scalpel blade support arm showing a circular scalpel blade mounted in parallel with and generally along the axis of the handle of the rotary scalpel of FIG. 1.

FIG. 51 is a top view of another modified scalpel blade support arm showing a circular scalpel blade mounted transversely of the axis of the handle of the rotary scalpel of FIG. 1 and generally rotating on or near the axis of the handle.

FIG. 52 is a schematic diagram of the electrical circuit of the rotary scalpel of FIG. 1.

DESCRIPTION OF THE PREFERRED EMBODIMENTS

Figure 3:
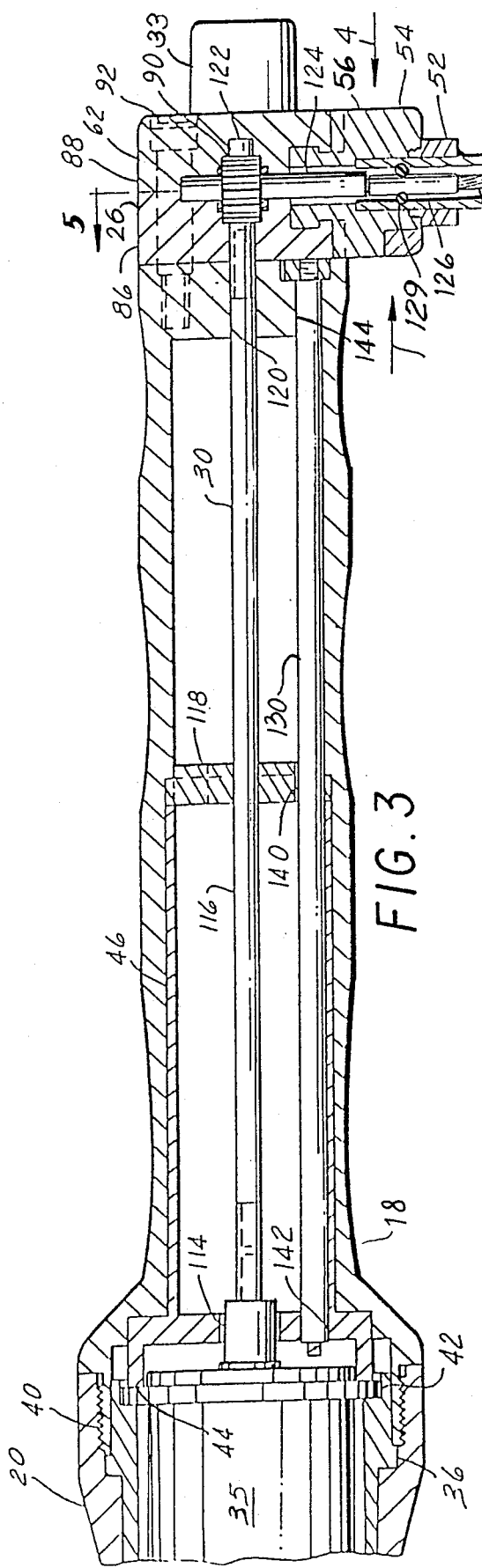
FIG. 3 is an enlarged, partial, longitudinal section view of the rotary scalpel shown in FIG. 1, taken substantially on the line 3—3 in FIG. 1.

The rotary scalpel structure 10 shown in FIGS. 1 and 2, is a power driven semi-automatic rotary scalpel. The rotary scalpel structure 10 as shown includes a handle 12, motor housing 14 to which an electrical connector 16 is secured and which is secured to the back end 18 of the handle 12 by the coupling 20. A circular scalpel blade support arm 22 is connected to the front end 24 of the handle 12 through the securing structure 26 and gear box 62 and supports on its outer end the circular scalpel blade 28.

Structure 30, best shown in FIG. 3, is provided extending through the handle 12 and blade support arm 22 for rotating the circular scalpel blade 28 on energization of the motor 35 in the housing 14. A light 32 is provided at the front end 24 of the handle 12 to illuminate the scalpel blade 28. Remote switch structure 34 extends through the handle 12 to close a switch at the back end 18 of the handle 12 to energize the motor 35.

More specifically, the handle 12 as shown in FIGS. 1 and 2 has an exterior configuration adapted to facilitate gripping of the handle by a surgeon. The handle 12 is a hollow cylindrical member substantially closed at the front end having longitudinal section configurations shown in FIGS. 3 and 7 and the end configurations shown in FIGS. 8 and 11.

The motor housing 14 as shown best in FIG. 3 is provided with a flange 36 thereon which is engaged by coupling 20 secured in a threaded connection 40 to the back end 18 of the handle 12 whereby the flange 42 on the motor 35 is held securely against the end 44 of the guiding and bearing member 46. The guiding and bearing member 46 which is cylindrical and shaped as shown in longitudinal section in FIG. 3, is positioned within the back end 18 of the handle 12 as will be considered in more detail subsequently.

The electrical connector 16 provides a two wire electrical connection to the rotary scalpel structure 10. One of the incoming wires is a hot wire and may for example provide current at 4 amps from a variac at 12 volts while the second wire may be a grounded wire as will be considered subsequently in conjunction with the circuit of FIG. 52.

As shown best in FIGS. 1,2,3 and 29, the blade support arm 22 is a hollow tubular member, the back end 48 of which is secured at the front end 24 of the handle 12 and on the front end 50 of which the circular scalpel blade 28 is mounted. Plunger member 52 of the blade and arm assembly permits securing the blade support arm 22 to the retaining structure 54 therefore.

Retaining structure 54 for securing the blade support arm 22 to the handle 12 through gear box 62 as illustrated best in FIGS. 19–22 includes a body member 56 shaped as shown to include an opening 58 therein for receiving the back end 48 of the blade support arm 22. The body member 56 further includes the annular flange 60 to prevent disengagement of the retaining structure 54 from the gear box 62 as will be considered subsequently and keys 62 to prevent rotation of the retaining structure 54 relative to the gear box 62.

Figure 19:
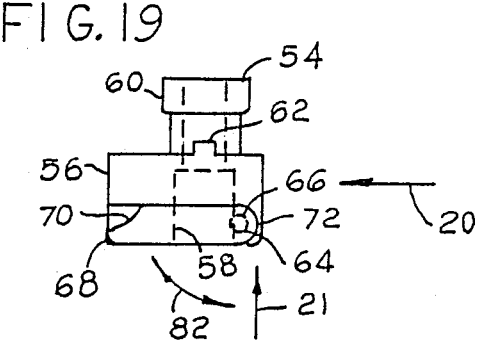
FIG. 19 is a back end view of the retaining structure for securing the blade support arm to the handle of the rotary scalpel structure shown in FIG. 1, taken substantially in the direction of arrow 19 in FIG. 3.
Figure 20:
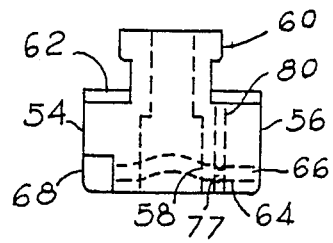
FIG. 20 is a top view of the structure illustrated in FIG. 19 taken in the direction of arrow 20 in FIG. 19.

Further, as shown best in FIG. 19, the retaining structure 54 is provided with a pin 64 extending through a passage 66 therein which is transverse of the opening 58 and extends thereinto radially. Pin 64 is rigidly secured to a lever 68 on the retaining structure 54 whereby on rotation of the lever 68 about the axis of the pin 64, the pin 64 is rotated about its own axis in the passage 66.

Figure 21:
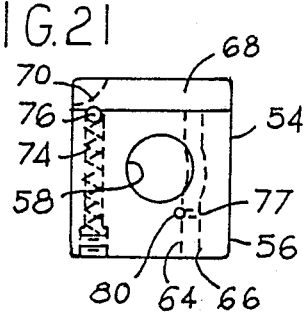
FIG. 21 is a side view of the structure illustrated in FIG. 19 taken in the direction of arrow 21 in FIG. 19.

Pin 64 is bowed slightly centrally along its longitudinal axis as shown in FIG. 21 to provide at the expense of some rotational resistance about its own axis an interference fit between the bowed section of the pin 64 and the plunger end 52 of the blade and arm assembly.

Rotation of the finger controlled lever 68 about the axis of the pin 64 is facilitated by the recess 70 in the lever 68 and the rounded end 72 on the lever 68. Free rotation of the lever 68 is inhibited by spring pressed detent structure 74 and a depression 76 in the lever 68 as shown best in FIG. 21.

Pin 64 has an annular groove 77 extending therearound which is traversed by a cylindrical retention pin 80 extending through the body member 56 transversely of the pin 64 and into the annular groove 77 as shown in FIG. 21. Thus, the pin 64 is allowed to rotate with the lever 68 but is prevented from being axially displaced from the body member 56.

Figure 22:
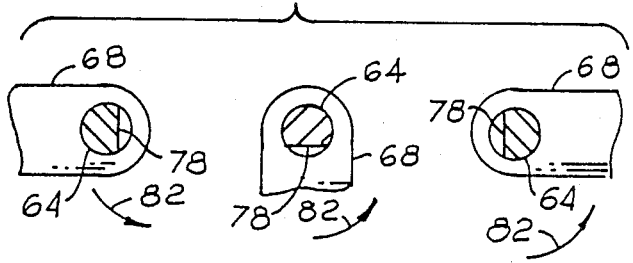
FIG. 22 is a composite figure showing three separate positions of the actuating member of the securing structure shown in FIG. 19 progressively showing the pin thereof in a locking position, an intermediate position and an unlocking position from left to right.

Further, as best shown in FIG. 22, the pin 64 is provided with a recess 78 in one side thereof which is so shaped that on rotation of the lever 68 into the position shown in FIG. 19, the recess 78 completely clears the opening 58 in the body member plunger 56, that is to say, no part of the pin 64 appears in the opening 58. However, with such structure, with the lever 68 rotated 180° in the direction shown by the arrows 82, the pin extends into the opening 58.

Figure 5:
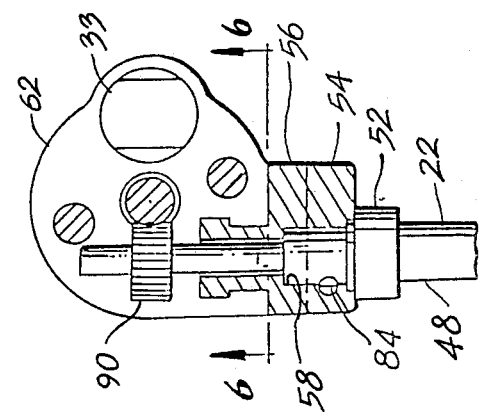
FIG. 5 is a cross section of the rotary scalpel shown in FIG. 1, taken substantially on the line 5—5 in FIG. 3.

Thus, referring specifically to FIG. 5, for example, the plunger end 48 of the blade support arm 22 may be inserted in the opening 58, with the lever 68 positioned 180° from its location shown in FIG. 19 to rotate the pin 64 into the position shown in FIG. 22 at the right wherein no portion of the pin 64 extends within the opening 58. The lever 68 is then rotated back into the position shown in FIG. 19 whereby the pin 64 is rotated into the position shown at the left in FIG. 22 through the intermediate position shown in the middle in FIG. 22 to provide a portion of the pin 64 positioned in the recess 84 in one side of the end of the plunger 52 of the blade support arm 22. The blade support arm 22 is thus connected to the body member 56 of the retaining structure 54 against displacement axially of the plunger 52 on the end 48 of the arm 22 and against angular rotation thereof relative to the body member 56.

Figure 23:
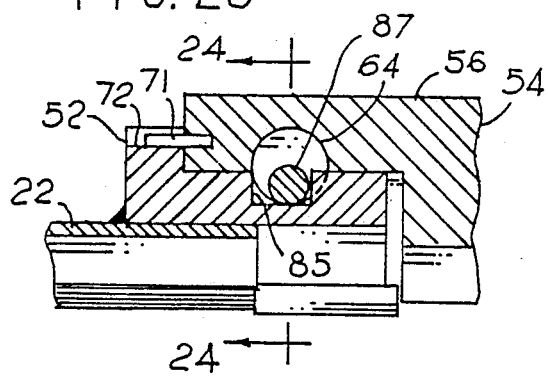
FIG. 23 is an enlarged elevation view of modified pin and shaft structure for use in the retaining structure illustrated in FIGS. 19-22.
Figure 24:
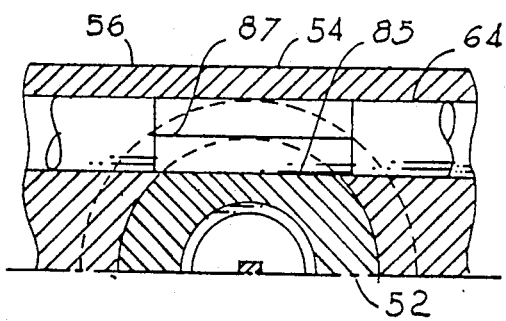
FIG. 24 is a section view of the pin and shaft structure illustrated in FIG. 23 taken substantially on the line 24—24 in FIG. 23.

Alternatively, as shown best in FIGS. 23 and 24, the end of plunger 52 of the blade support arm 22 is provided with a semi-rectangular recess 85 therein and the pin 64 is provided with an eccentric cam portion 87 centrally thereof. With such structure in one position of the lever 68 as for example the position shown in FIG. 19, the eccentric cam portion 87 of the pin 64 is in engagement with the end of the plunger 52 on the blade support arm 22 within the recess 85 as shown best in FIG. 23 to lock the plunger 52 on end 48 of the blade support arm 22 to the retaining structure 54. With the lever 68 rotated 180° the eccentric cam portion 87 of the pin 64 in FIG. 23, will completely clear the recess 85 and allow the plunger 52 on the end 48 of the blade support arm 22 to be removed from the retaining structure 54.

As shown in FIG. 13, the lever 68 and spring detent means 74 may be replaced by lever 79 and spiral spring 81. Spiral spring 81 urges the lever in a direction to engage the cam portion 87 on pin 64 into eccentric interference engagement with the bottom of recess 85 as shown in FIG. 23.

A single pin 71 is secured to the body member 54 and fits within opening 73 in plunger 52 to permit securing the support arm 22 to the handle 12 in only one relative position with respect thereto.

Figure 25:
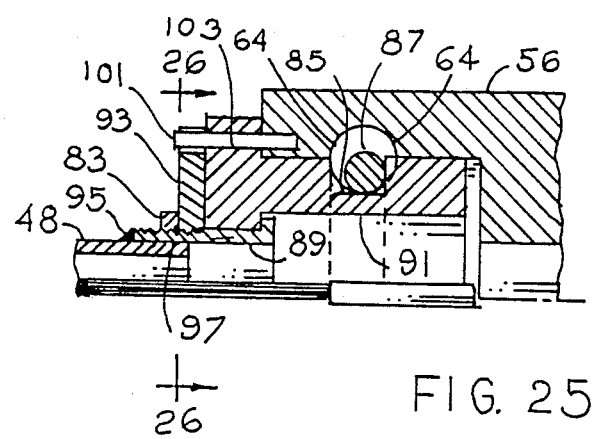
FIG. 25 is a section view of another modification of the retaining structure shown in FIGS. 19-24.
Figure 26:
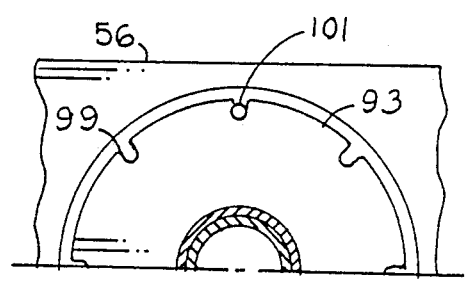
FIG. 26 is section view of the modified retaining structure illustrated in FIG. 25 taken substantially on the line 26—26 in FIG. 25.

In a still further modification of the retaining structure 54 as shown in FIGS. 25 and 26, a separate annular adjusting structure 89 is rigidly secured to the end 48 of the blade support arm 22 as by welding or the like. A further securing member 91 having the longitudinal cross section as shown best in FIG. 25 is rotatably secured to the adjusting structure 89. If desired, the portion 93 of the adjusting structure 89 may be threadedly secured on the portion 95 thereof by a threaded connection 97 therebetween and locked in place with nut 83 to facilitate assembly of the adjusting structure 89 and the securing member 91 as shown in FIG. 25. Further, in accordance with the modification of the invention, as shown in FIGS. 25 and 26, the portion 93 of the adjusting structure 89 is provided with angularly spaced apart radially extending slots 99 in the periphery thereof and a long locating pin 101 is rigidly secured to the body member 56 of retaining structure 54.

Thus, in the method of use of the modified retaining structure 54, a single opening 103 in the securing member 91 is aligned with a selected radially extending slot 99 in the adjusting member 89 and the securing member 91 on the end 48 of the blade support arm 22 is inserted into the body member 56 of the retaining structure 54 as before with the pin 101 extending through both the single opening 103 in the securing member 91 and the selected slot 99 in the adjusting member 89. The securing member is then locked in position by rotation of the lever 68 and a pin 64 as before.

With such method of operation and with the structure shown in FIGS. 25 and 26, the blade support arm 22 thus assumes an angle about the axis of the end 48 thereof chosen by the selection of the particular radially extending slot 99. Accordingly, with the structure shown in FIGS. 25 and 26, the position of the circular rotary scalpel blade 28 with respect to the handle 12 of the rotary scalpel structure 10 may be selected through substantially 360° about the end 48 thereof at different locations depending only on the number of slots 99 provided in the adjusting structure 89. In the particular embodiment of the invention shown in FIGS. 25 and 26, eight slots 99 are provided as shown so that the angular position of the end 48 of the blade support arm 22 may be adjusted in 45° increments about the end 48 thereof.

Figure 4:
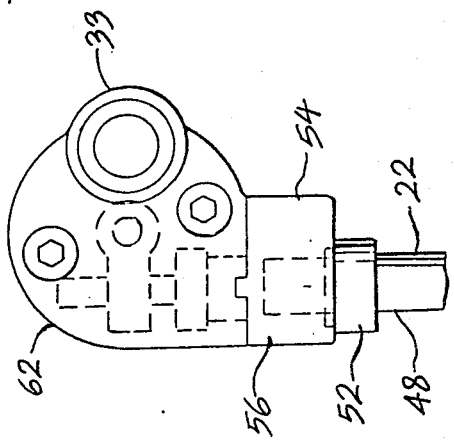
FIG. 4 is an end view of the portion of the rotary scalpel of FIG. 1, shown in FIG. 3, taken in the direction of arrow 4 in FIG. 3.
Figure 6:
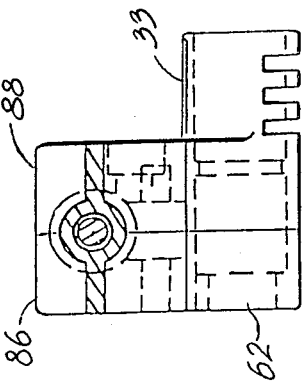
FIG. 6 is a cross section of the rotary scalpel shown in FIG. 1, taken substantially on the line 6—6 in FIG. 5.

As shown best in FIGS. 4, 5 and 6, the retaining structure 54 is held in place on the end 24 of the handle 12 by the gear box 62. The gear box 62 is split into two separate halves 86 and 88 positioned with respect to the handle 12 as shown best in FIG. 3. In assembly, the worm and worm gear structure 90 as shown best in FIGS. 3, 5 and 7, is positioned in the gear box 62 along with the securing structure 54 and the gear box 62 is secured to the end 24 of the handle 12 by convenient means such as screws 92 engaging threaded holes in the end of the handle 12. The housing 33 for light 32 is constructed integrally with the gear box 62, and supports light 32 for illumination of the circular scalpel blade 28 as shown best in FIG. 1.

As shown best in FIG. 29, the circular scalpel blade 28 is mounted on the end 92 of a shaft 94 rotatably mounted in a pressed fit self lubricating, preferably sintered graphite and brass bearing 96 which is pressed into the end 50 of the tubular blade support arm 22. Shaft 94 is connected by means of a non-circular recess 98 in the end thereof to the non-circular end 100 secured to the end 102 of a flexible drive wire 104 extending through the blade support arm 22. Thus, in operation as the flexible drive wire 104 is rotated, the shaft 94 is rotated in the bearing 96 to rotate the circular scalpel blade 28.

Circular scalpel blade 28 is secured to the end 92 of the shaft 94 by abutment thereof against a dish shaped resilient washer 106 which urges the scalpel blade 28 outwardly of the shaft 94 and the resilient C-ring 108 positioned within the annular recess 110 around the end 92 of the shaft 94. Relative rotation between the shaft 94 and the circular scalpel blade 28 is prevented by means of the key 112 extending into both the circular scalpel blade 28 and the shaft 94.

Optionally, since the tubular blade support arm assembly 22 is subjected repeatedly to sterilization by the flash method, or autoclave method, and lubricant may be used within the tubular arm 22 to minimize friction with the rotating braided flexible drive wire 104, seals, preferably of the synthetic rubber "O" ring type 95, and 131 may be added as shown in FIGS. 3 and 29 located in their respective grooves machined in the shaft 94 and bearing 96 and in the end 48 of tubular arm 22 and the flexible drive wire end 126 rotating within the plunger.

Rotation of the flexible drive wire 104 is accomplished on energizing of the motor 35 to rotate the motor shaft 114. Rotation of the motor shaft 114 produces rotation of the shaft 116 extending through the guiding and bearing member 46 and the central bearing disc 118 assembled in the handle 12 as shown in FIG. 3 and the passage 120 through the end 24 of the handle 12. A right angle worm and worm gear drive structure 90 is secured to the end 122 of the shaft 116 and the shaft 124 extending perpendicularly thereto in the gear box 62. Rotation of the shaft 30 causes rotation of the shaft 124 through the worm and worm gear structure 90. Shaft 124 again has an axially extending non-circular opening therein into which a non-circular connector 126 of the flexible drive wire 104 extends. Flexible drive wire 104 is thus rotated on rotation of the shaft 124. Accordingly, when the motor 35 is energized, the circular scalpel blade 28 is rotated.

The remote switch structure 34 as shown best in FIGS. 3, 7, 8 and 10 includes a cylindrical shaft 130 having non-circular ends 134 and 136 which extends through the length of the handle 12 and through passage 140 in the bearing disc 118 and guiding and bearing member 46, passage 142 in the guiding and bearing member 46 and passage 144 in the end 24 of handle 12. Switch structure 34 further includes the actuating member 146 shaped as shown best in FIG. 8, having a non-circular opening 148 therethrough and the S-shaped spring 150. At the other end of the shaft 130, an electrical connector 152 is also connected by means of a non-circular opening 155 therethrough to the non-circular end 136 of the shaft 130. The end 156 of the spring 150 is rigidly secured in the end 24 of the handle 12.

Thus, in operation of the remote switch structure 34, the actuating member 146 is normally urged counter-clockwise against the stop 158 formed in the end 24 of the handle 12. On pressing of the actuating member 146 it rotates about the axis of the shaft 130 with the shaft 130 against the bias of the spring 150 to produce rotation of the electrical connector 152 to close the circuit switch structure 34 shown in FIG. 52 to provide power to the motor 35.

On release of the actuating member 146, spring 150 returns the electrical connector 152 to its original position opening the circuit to the motor 35.

Thus, through the structure 34, electrical switching on and off of the motor 35 may be accomplished from the front end of the handle while the actual electrical switching takes place at the back end of the handle. This satisfies requirements for manual dexterity of the surgeon and removal of electrical switching from the tissue in which an incision is required.

Alternatively, and as best shown in FIGS. 13-16, the switch structure 34 may be replaced by switch structure 155. Switch structure 155 includes the manually operable switch member 157 secured to the gear box 62 by convenient pivot mounting means 159 for manual pivotal movement about the pivot means 159 in the direction of arrow 161 in opposition to the bias of spring means 153. The switch structure 155 further includes the elongated rod 163 extending longitudinally of the handle 12 through the end 24 of the handle 12 and through the guiding and bearing structure 46 as before. A flexible, linear switch 165 as shown in FIGS. 15 and 16 is provided at the back end 18 of the handle 12 which includes a cylindrical portion 167 passing through the guiding and bearing structure 46 at the end 18 of the handle 12 which is connected to the end 169 of the rod 163 by convenient means such as threads or pin and socket connection 171. A further pin and socket connection 173 is provided between the switch member 157 and end 175 of shaft 163.

As shown best in FIG. 15, a U-shaped electrical contact 179 constructed of laminar spring material is secured to the back end of the guiding and bearing structure 46 by convenient means such as rivets 145 and includes a central portion 147 which is raised from the end of the guiding and bearing structure 46 as shown in FIG. 16. A straight electrical spring contact 177 is also secured to the back end of the guiding and bearing structure 46 as by rivet 143 at one end thereof. The other end of the electrical contact 177 extends under the raised central portion 147 of electrical contact 179 and is between electrical contact 179 and the cylindrical switch portion 167, whereby on movement of shaft 163 to the left in FIG. 16, the cylindrical switch portion 167 moves the free end 151 of switch contact 177 into engagement with contact 179 to close the switch structure 165. The switch contacts 177 and 179 are connected to electrical conductors 164 and 166 respectively, through appropriate conductive straps 181 and 183 and locator 141 as before, located in the guiding and bearing structure 46 and housing 14.

The conductors 164 and 166 are separated in the housing 14 but as they pass through the end 185 of the housing 14, they are encased in a single outer insulation member 187, as shown in FIGS. 13 and 16. Further as shown in FIGS. 13 and 16, the conductors 164 and 166 along with the outer insulation 187 therefore are protected from the sharp edges of the opening 189 through the end 185 of the housing 14 by a wire protector member 191.

In accordance with the invention, the wire protector 191 i of a flexible material such as rubber and is cylindrical and hollow and has at its opposite ends the donut shape flanges 193 and 195, as shown best in FIGS. 17 and 18. With the wire protector 191 in position in the opening 189 in which it can be inserted by deformation of the flexible wire protector, possible due to the inclusion therein of a longitudinally extending slot 201 therein, the conductors 164 and 166 and insulation 187 can be passed through the opening 199 in the wire protector 191 and are thus insulated from the sharp edges of the opening 189 through the back 185 of the housing 14.

In operation of the modified switch structure 155, if a surgeon desires to actuate the motor 35 to drive the rotary circular scalpel blade 28, he has only to move the switch member 157 in a clockwise direction as shown in FIG. 13 by arrow 161 with his finger to cause the shaft 163 to move to the left in FIG. 13 which will cause engagement of the end 151 of switch contact 177 with the contact 179 to complete an electrical circuit through the motor 35. A finger guard protective ridge 141 is provided on switch member 157 to prevent the index finger from slipping forward in the direction of the blade and arm assembly 22.

On release of the switch member 157 the spring bias member 153 causes the switch member 157 to move in a counterclockwise direction which in turn moves the shaft 163 to the right in FIG. 13 and breaks engagement of the contact 177 with the contact 179 to break the electrical circuit through the motor 35 and thus stop the motor.

Referring more specifically to the electrical circuit 162, shown in FIG. 52, it will be noted that the center conductor 164 is a ground line while conductors 166 and 168 are connected to a single hot or high voltage input connector. The conductor 164 and the conductor 168 go directly to the lamp 32 whereby when electrical power is connected to the circular scalpel 10, the light 32 is always lit, providing illumination for the scalpel blade 28. The remote switch structure 34 shown schematically in FIG. 52 then opens and closes the conductors to the motor 35 through the hot line 166 and the ground 164.

The conductors 164, 166 and 168 as shown in FIGS. 8 through 12 are essentially conducting straps which make sliding contact with each other between the handle 12 and the guiding and bearing member 46. Bayonet connectors 169 are provided between the housing 14 and the guiding and bearing member 46, while electrical spade connectors 171 are provided between the electrical connector 16 as shown in FIGS. 1 and 2, and the housing 14. Thus, easily manufactured positive electrical connections are provided throughout the embodiment 10 of the powered circular scalpel structure of the invention.

Referring more specifically to FIG. 27, the circular scalpel blade 28 is a substantially flat disc having the opening 172 extending axially through the middle thereof and having the outer periphery 174 sharpened. Both sides 176 and 178 of the circular scalpel blade 28 are concave as shown best in FIG. 28, whereby friction of the material being cut against the scalpel blade 28 is materially reduced during use of the rotary scalpel structure 10.

In operation of the circular scalpel structure 10, for best results in minimizing formation of scar tissue at the start and indeed all along an incision, it has been found that driving the rotary scalpel blade 28 at a peripheral speed of between 4 and 7 centimeters per second is particularly desirable. Thus, the speed of the motor 34, the gear reduction in the motor and of the worm and worm gear structure 90 and the diameter of the circular scalpel 28 have been chosen to provide such a peripheral speed. Other peripheral speeds may of course be provided when considered suitable for specific surgical conditions.

The modified circular thin scalpel blade structure shown in FIG. 30 includes the sharpened symmetrically angled outer edge 179 and the inner hub 181 adapted to fit over the end 92 of the shaft 94 and to be secured thereto for rotation therewith as shown in FIG. 29. The modified circular scalpel blade 183 however includes a circular depressed portion 185 on both sides thereof centrally positioned with respect to the outer periphery 179 and hub 181. The depressed portions 185 of the thin rotary scalpel blade 183 greatly reduce frictional resistance to tissue passage and tissue pick-up during the passage of the circular rotary scalpel blade 183 through tissue being incised thereby. The blade 183 is particularly useful in effecting deep cuts.

In the embodiment of the blade 183, the edge angle found preferable in actual incisions is small, i.e. of the order of 10%, and the overall width of the blade at the wider section of the edge is 0.36 mm while the circular depressed section is only 0.26 mm thick. Also, it is preferable to provide an angle, reverse to the edge angle, i.e. between the edge 179 and the depressed portions 185 of the blade 183 which is less sharp than the edge angle. An angle of 45% is found to reduce scar tissue.

The modified circular rotary scalpel blade 187 shown in FIG. 31 again has an outer sharpened periphery 189 and an inner circular hub 191. The rotary scalpel blade 187 however includes a central portion 193 which is substantially flat from the hub 191 to the outer periphery 189. An annular recess 195 which as shown has a gradually sloping radially inner side and a steeper sloping radially outer side is provided adjacent the outer periphery 189 on both sides of the scalpel blade 187. The grooves or recesses 195 again reduce drag and separated tissue pick-up as the rotary scalpel blade 187 passes through tissue to be incised. The flat portion 193 of the blade 187 and the fact that the outer periphery 189 and recesses 195 are formed from a similarly dimensioned flat portion makes the rotary scalpel blade 187 particularly cheap to machine and heat treat. The recesses 195 reduce drag sufficient for many uses. The blade 187 is particularly useful in effecting shallow cuts.

Also as shown in FIGS. 30 and 31, the blades 183 and 187 are constructed with a recess in the hub portions 181 and 191 and radially extending openings through the hub portions for receiving pins extending through the hubs and shaft ends received in the recesses to secure the blades 183 and 187 to the shafts.

As shown in FIG. 32, any of the circular rotary scalpel blades such as blade 28 and the modified blades 183 and 187 may be part circular or notched. The particular modified circular rotary scalpel blade 197 shown in FIG. 32 is provided with three notches 199 evenly spaced angularly therearound as shown. Blades such as the rotary scalpel blade 197 may be sharpened on all of their edges as shown or may be sharpened on only the leading edge, that is, one side of the notch 199, depending on which way the blade is rotated or on both sides of the notch to permit rotation of the blade in either direction in combination with or without sharpening of the entire outer periphery thereof. The portion of the notched circular rotary blade 197 which is sharpened will depend on the particular use of the blade 197 and the drive capabilities thereof in use.

The rotary scalpel blades 205 and 207 illustrated in FIGS. 33 and 34 are flat linear blades which extend radially from a shaft such as shaft 94 as shown in FIG. 28 and as particularly shown in FIG. 35. The linear blades 205 and 207 as shown in FIGS. 33 and 34 have a single edge sharpened and are sharpened on both edges respectively.

The blades 205 and 207 may be provided with a hub and secured to the shaft 92 in the manner shown in FIG. 35. Alternatively, the blades 205 and 207 may have the hub and pin retention structure considered above.

However, the linear blades 205 and 207 shown in FIGS. 33 and 34 are substantially flat over the entire length thereof and have conventional slot like openings 209 through their inner ends. These blades may be secured to a hub by blade mounting structure including a generally T-shaped member having a cylindrical stem portion and a rectangular cross bar and a spring biased second generally T-shaped member having a raised portion complementary to the opening in the blades and positioned in the first T-shaped member. Retaining pins extend across the open side of the cross bar of the first T-shaped member.

Intermittent cutting with the rotary driven radially extending linear scalpel blades 205 and 207 is accomplished by the rotary scalpel structure of the invention utilizing the blades 205 and 207 as shown in FIGS. 35 and 36.

In use the second T-shaped member may be moved upwardly against bias of the spring by a separate member inserted through the pins. The end of a blade is then inserted in the cross bar portion of the first T-shaped member and the protection on the second T-shaped member allowed to pass through opening 209 in the blade to lock the blade to the blade mounting structure against the pins.

A blade guard 211 must be utilized with the rotary scalpel structure 10 of the invention to protect a blade such as blade 205 in use therewith when for example the rotary scalpel structure 10 is rested on a hard surface. The blade guard 211 mostly protects the surgeon and the strips of epidermis being separated from the subjacent tissue with the rotary radial scalpel blade 205 in all but the selected area where the separation of strips by the blade 205 is desired.

As shown, the blade protector 211 is part circular in plan view with an opening of approximately 140° on top and may be less at the bottom of which the opened edge is slightly curled towards the blade but without touching it to facilitate forward progress as the blade operates. The blade guard 211 as shown best in FIG. 35 has a generally U-shaped cross section. An opening 213 is provided in one side of the blade guard 211 and an axially split flange 215 is provided extending from the opening 213 as shown best in FIG. 35. The flange 215 is adapted to fit around the end 50 of the tubular blade support arm 22 and is clamped thereto by the annular clamp 217 and set screw 219. The blade guard 211 may be constructed of suitable plastic, metal or the like, again depending on the particular use to which the rotary scalpel 10 will be put and the pressure exerted on its bottom face.

The blade protector structure 200 shown in FIGS. 37 and 38 includes a flat hollow disc 202 having a stem 204, which is also hollow, extending from one side thereof. The disc and stem are split axially along line 206 and are held together at one side by a living hinge 208 constructed of the same plastic as the disc and stem.

The circular scalpel blade 28 or any of blades 183, 187 and 197 may be placed in the disc shaped recess 210 formed in the flat disc portion 202 of the blade protector structure 200 with the halves of the protector separated by bending the living hinge 208. The protector 200 is then reformed in the configuration shown in FIGS. 37 and 38 and a hollow cylinder 212 which is split at 214 axially along one side thereof is positioned with an intereference fit over the stem 204 to hold the protector in a closed position.

The cylinder 212 is constructed of resilient plastic and the internal diameter thereof is slightly smaller than the external diameter of the stem 204 of the blade protector 200.

Thus, with the structure illustrated in FIGS. 37 and 38, a circular scalpel blade may be easily transported and moved about without danger of damaging the scalpel blade periphery or cutting someone.

The blade protector or guard 221 illustrated in FIGS. 39-41 is again intended to protect circular scalpel blades such as blades 28, 183, 187 and 197 and may be utilized to protect the blades in assembly on rotary scalpel structure. The blade protector 221 is constructed of plastic and has the plan view shown best in FIG. 39 including transverse slots 223 extending therethrough which are narrower at the open end 225 of the slots than they are at the inner end 227 of the slots and thus fits snugly around the hub section 181 of the blade 185, for example. As shown best in FIGS. 40 and 41, the blade protector structure 221 has an internal recess 229 therein shaped to receive the substantially flat portion of a rotary scalpel blade with the hub of the blade and the end 50 of a blade support arm extending through the slots 223. A tab portion 231 is provided on the blade protector 221 to facilitate removal of the blade protector 221 by gripping the blade protector 221 by the tab 231 while holding the arm 22 and blade assembly of the scalpel with the other hand.

In use the blade protector 221 is inserted over the circular scalpel blade it is desired to protect by spreading the outer end 225 of the slots 223 to allow the hub of the blade and/or the outer end of a blade support arm to pass therethrough into the larger inner end 227 of the slots 223. To this end the blade protector 221 is constructed of plastic material or the like which is sufficiently resilient to permit passage of blade hubs and blade support arms into the lower end 227 of the slots 223 where they are retained until the blade protector 221 is physically removed therefrom by again spreading the end 225 of the slots 223 by pulling on the tab 231. Thus, when in place, the protector is loosely fitted around the blade allowing sterilization to take place with the protector in place.

Alternatively, to protect the blade edge from rubbing the sterilization tray during flash or steam sterilization the blade support arms 22 may be supported when the rotary scalpel structure 10 is layed down by a blade support arm stand 233 as shown in FIG. 42. The blade support arm stand 233 is of bent spring wire or bent narrow stainless steel thin strip construction and is formed in wire as shown in FIGS. 43-45. As shown in FIGS. 43-45, the blade support arm stand 233 includes a lower U-shaped arcuate portion 235 for supporting the stand on a flat surface in an upright position. The blade support arm stand 233 is further provided with an upper portion 237 which is generally circular and extends for more than 180° and is terminated with a reversed hook portion 239 to prevent the sharp edge of the wire or strip end from scratching the blade structure. As shown best in FIGS. 42 and 44, the end 50 of the blade support arm is positioned in the upper portion 237 of stand 233 with the stand 233 in use by slightly springing the upper portion 237. The hook portion 239 of the stand 233 permits easy insertion of the blade support arm in the portion 237 of the stand. For stability the lower end 235 and upper end 237 of the blade support arm stand 233 are positioned substantially at right angles to each other as shown in FIGS. 43 and 44 and are connected by a reverse curved central portion 241 extending therebetween shown best in FIG. 44.

Another modified and extremely simple blade protector is shown in conjunction with a circular scalpel blade 28 on the blade support arm 22 in FIGS. 42, 46 and 47. The blade protection structure 243 is a flat, square sheet of flexible material such as foamed plastic having a narrow annular tacky adhesive section 247 on one side 245 thereof only. The blade protector 243 which is sufficiently large to extend beyond the outer periphery of the rotary scalpel blade which it is protecting as shown in FIG. 46 is merely adhered to the blade 28 on one side thereof as shown best in FIGS. 46 and 47. The blade 28 is thus protected from engagement with objects which may dull the periphery thereof and is prevented from harming individuals or material which may come in contact with the blade protector and which might otherwise come in contact with the sharp periphery of the blade. When it is desired to use the blade 28, the blade protector 243 is merely peeled off of the blade 28. Of course, due to the nature of the material from which the blade protector 243 is made, limited reuse of the blade protector is possible. Also, the nature of the adhesive may be such as to assure that the protector may be compatable with any of the sterilization procedures in use, i.e. steam (hot), gas (room temperature), etc. and would also allow its availability in sterile packages.

As shown in FIGS. 48 and 49, depth limiting structure or stop 251 is utilized in conjunction with the rotary scalpel 10 to limit the depth of incision made. The depth limiting structure 251 may be constructed of plastic, metal or other suitable material. The depth limiting structure 251 includes a lower sled like portion 253 adapted to slide in either direction on tissue to be cut 263 in a plane perpendicular to the scalpel blade 28 and to this end includes curled ends 255 and 257. The depth limiting structure 251 further includes an upper portion 259 which is in the form of a split cylinder having an axis extending perpendicularly to the blade 28 which split cylinder extends for approximately 220° and is adapted to be sprung over the end 50 of the blade support arm structure 22 as shown in FIGS. 48 and 49. The portions 253 and 259 of the depth limiting structure 251 are connected by straight central portion 261. If necessary the sled like portions may extend around the blade cutting plane to apply the same amount of sled pressure on both sides of the incision on the tissue being incised, thus promoting future balanced healing on both sides of the incision.

In use, the depth limiting structure 251 connected to end 50 of the blade support arm 22 is moved along the surface of tissue to be cut and limits the depth of cut which may be made in the tissue with a rotating scalpel blade attached to the blade support arm as shown best in FIG. 49.

The modification of the circular scalpel structure 10 illustrated in FIG. 51 includes a modified circular blade support arm 222. Similarly, the modification of FIG. 51 includes a further modified blade support arm 222 as will be seen from a comparison of FIGS. 50 and 51. The support arms 22, 220 and 222, respectively, support a circular scalpel blade 28 at an angle of 15° to the axis of the circular scalpel 10, as shown in FIG. 13, and parallel and transverse to the axis of the handle of the circul scalpel 10, respectively. Each of the circular scalpel blade centers in FIGS. 51 and 52 are positioned on the axis of the handle of the circular scalpel 10.

The different support arms 22, 220 and 222 each loop around the incision area to provide a cleared area between the end of the handle and the scalpel blade so that the surgeon has maximum visual access to an incision being made.

Furthermore, as shown in FIG. 50, the distance 159 between the center of the powered rotary blade and the top of the operators index finger resting on switch 157 is such as to duplicate or approach the 4 to 5 centimeters corresponding to index finger to blade distance existing and accepted through training on conventional linear scalpels. This assures maintenance of acquired skills and habits of the operating surgeon.

Specifically, with the support arm 22, the support arm is secured to the retaining structure 54 and extends in a circular arc for approximately 135° after which it extends straight to the intersection of the support arm and the axis of the handle of the circular scalpel 10. With the structure of FIG. 50, the support arm extends initially in a full 180° circular arc and then straight to the axis of the handle of the circular scalpel 10. The structure of FIG. 51 is slightly different in that it first extends approximately 135° in a circular arc, then extends for a short straight portion followed by a reverse curvature of 45° to the axis of the handle of the circular scalpel 10. The support arm 22 may take other configurations however the 4 to 5 centimeter spacing between the index finger and blade should be maintained.

While different embodiments of the invention and modifications thereof have been considered in detail, it will be understood that other modifications and embodiments are contemplated by the inventor. For example, the powered rotary scalpel may be powered by a battery positioned in a rearward extension of the handle thereof. Also, dual, transversely spaced apart rotary blades may be provided on the same scalpel to facilitate cutting of skin strips if desired. The circular blades can also feature a sawtooth pattern on their edges while retaining concave or depressed centers or any of the unique configurations described herein. It is the intention to include all such embodiments and modifications as are defined by the appended claims within the scope of the invention.

I claim:

1. A circular rotary scalpel blade including a hub portion having an opening therethrough for mounting the scalpel blade on a rotating member for rotatably driving the scalpel blade, a substantially flat portion extending radially outwardly from the hub portion, a sharpened, radially outer, peripheral edge having smooth and slightly concave sides and an annular groove between the flat portion and peripheral edge os the rotary scalpel blade on each side thereof having sides including a greater slope adjacent the outer peripheral edge of the rotary scalpel blade and a lesser slope adjacent the substantially flat portion of the rotary scalpel blade and being less than one quarter of the radial extend of the blade in transverse dimension.

2. A rotary scalpel blade including a sharpened edge, means for mounting the scalpel blade on a rotating member for rotatably driving the scalpel blade, a blade protector in combination with the rotary scalpel blade including a flat, hollow disc centrally split in an axial direction, a living hinge at one end of the split in the flat disc and means for securing the split, flat, hollow disc together with a circular blade therein comprising a smaller diameter stem extending from one side of the disc axially thereof and an axially split hollow cylinder having an internal diameter slightly less than the external diameter of the stem positioned over the disc stem.

3. A rotary scalpel blade including a sharpened edge, means for mounting the scalpel blade on a rotating member for rotatably driving the scalpel blade and a blade protector in combination with the rotary scalpel blade including a plastic envelope having a recess centrally thereof and opened at one end including slots extending into the one end of the envelope which slots are wider at the bottom than at the top, constructed of flexible material whereby a rotary scalpel blade may be positioned within the recess with a blade support arm and/or blade hub projecting out of the slots therein on flexing of the blade protector to increase the opening at the top of the slots.

4. Structure as set forth in claim 3, and further including a tab portion on the envelope member for facilitating placing a rotary scalpel blade in the blade protector and removing the blade protector therefrom.

5. A substantially flat, circular scalpel blade including a smooth sided sharpened edge having a substantially V-shaped cross section at the outer periphery thereof and at least one, at least partially depressed side immediately radially inwardly of the sharpened outer periphery to reduce frictional resistance to movement of the periphery of the blade through tissue including an annular recess immediately adjacent the sharpened edge of the scalpel blade having a steeply sloping side toward the outer periphery of the scalpel blade and a gently sloping side toward the center thereof, which annular recess is less than one quarter the radius of the scalpel blade in transverse dimension, and means for mounting the scalpel blade on a rotatable member for rotating the scalpel blade in use including an opening through the center of the scalpel blade.

* * * * *

UNITED STATES PATENT AND TRADEMARK OFFICE
CERTIFICATE OF CORRECTION

PATENT NO. : 4,899,742

DATED : February 13, 1990

INVENTOR(S) : George H. Muller

It is certified that error appears in the above-identified patent and that said Letters Patent is hereby corrected as shown below:

Column 11, line 17, "10%" should read --10°--.

Column 11, line 23, "45%" should read --45°--.

Signed and Sealed this

Thirteenth Day of August, 1991

Attest:

HARRY F. MANBECK, JR.

*Attesting Officer*  Commissioner of Patents and Trademarks